United States Patent
Nelissen et al.

(10) Patent No.: US 12,233,172 B2
(45) Date of Patent: Feb. 25, 2025

(54) HEATING APPARATUS AND METHODS

(71) Applicant: ACADEMISCH ZIEKENHUIS LEIDEN (H.O.D.N. LUMC), Leiden (NL)

(72) Inventors: Rob Nelissen, Leiden (NL); Bart Pijls, Leiden (NL)

(73) Assignee: ACADEMISCH ZIEKENHUIS LEIDEN (H.O.D.N. LUMC), Leiden (NL)

( * ) Notice: Subject to any disclaimer, the term of this patent is extended or adjusted under 35 U.S.C. 154(b) by 274 days.

(21) Appl. No.: 17/276,583

(22) PCT Filed: Sep. 26, 2019

(86) PCT No.: PCT/NL2019/050649
§ 371 (c)(1),
(2) Date: Mar. 16, 2021

(87) PCT Pub. No.: WO2020/067898
PCT Pub. Date: Apr. 2, 2020

(65) Prior Publication Data
US 2022/0047733 A1   Feb. 17, 2022

(30) Foreign Application Priority Data

Sep. 26, 2018 (NL) ........................ 2021715
Sep. 27, 2018 (NL) ........................ 2021722

(51) Int. Cl.
*A61L 2/04* (2006.01)
*A61K 31/165* (2006.01)
(Continued)

(52) U.S. Cl.
CPC .............. *A61L 2/04* (2013.01); *A61K 31/165* (2013.01); *A61K 31/357* (2013.01);
(Continued)

(58) Field of Classification Search
CPC ..... A61L 2/04; A61L 2/18; A61L 2/26; A61L 2202/16; A61L 2202/21; A61N 1/403;
(Continued)

(56) References Cited

U.S. PATENT DOCUMENTS 5,254,117 A    10/1993  Rigby et al.
6,229,126 B1 *  5/2001  Ulrich ............... H05B 6/40
                                                   219/662
(Continued)

FOREIGN PATENT DOCUMENTS

CN    102631690 A    8/2012
CN    204446661 U    7/2015
(Continued)

OTHER PUBLICATIONS

M.G.E. Oldhoff et al., "Comparision in clinical performance of surgical guides for mandibular surgery and temporomandibular joint implants fabricated by additive manufacturing techniques", Journal of Mechanical Behavior of Biomedical Materials, vol. 119, Published 2021 (Year: 2021).*
(Continued)

*Primary Examiner* — Jennifer Wecker
*Assistant Examiner* — Brady C Pilsbury
(74) *Attorney, Agent, or Firm* — Harness, Dickey & Pierce, P.L.C.

(57) ABSTRACT

A medical inductive heating apparatus (10) for heating at least a portion of a prosthetic or implant. The apparatus (10) has at least one external induction coil, the external induction coil being external to a body or housing of the apparatus (10). The coil (12) is sized and dimensioned to be smaller than a body portion associated with the prosthetic or implant.

21 Claims, 6 Drawing Sheets

(51) Int. Cl.
| | |
|---|---|
| *A61K 31/357* | (2006.01) |
| *A61K 31/407* | (2006.01) |
| *A61K 31/4178* | (2006.01) |
| *A61K 31/427* | (2006.01) |
| *A61K 31/496* | (2006.01) |
| *A61K 31/7036* | (2006.01) |
| *A61K 31/7048* | (2006.01) |
| *A61K 31/7056* | (2006.01) |
| *A61K 38/12* | (2006.01) |
| *A61K 38/14* | (2006.01) |
| *A61L 2/18* | (2006.01) |
| *A61L 2/26* | (2006.01) |
| *A61N 1/40* | (2006.01) |

(52) U.S. Cl.
CPC ........ *A61K 31/407* (2013.01); *A61K 31/4178* (2013.01); *A61K 31/427* (2013.01); *A61K 31/496* (2013.01); *A61K 31/7036* (2013.01); *A61K 31/7048* (2013.01); *A61K 31/7056* (2013.01); *A61K 38/12* (2013.01); *A61K 38/14* (2013.01); *A61L 2/18* (2013.01); *A61L 2/26* (2013.01); *A61N 1/403* (2013.01); *A61L 2202/16* (2013.01); *A61L 2202/21* (2013.01)

(58) Field of Classification Search
CPC .... A61N 1/406; A61K 31/165; A61K 31/357; A61K 31/407; A61K 31/4178; A61K 31/427; A61K 31/496; A61K 31/7036; A61K 31/7048; A61K 31/7056; A61K 38/12; A61K 38/14

See application file for complete search history.

(56) References Cited

U.S. PATENT DOCUMENTS

| | | | |
|---|---|---|---|
| 6,238,421 B1 | 5/2001 | Gunther et al. | |
| 6,786,904 B2 * | 9/2004 | Doscher | A61B 18/04 623/902 |
| 7,729,778 B2 * | 6/2010 | Eggers | A61F 2/82 607/116 |
| 2011/0251687 A1 | 10/2011 | Prescott | |
| 2013/0123613 A1 * | 5/2013 | Trembly | A61B 6/12 600/12 |
| 2015/0157872 A1 * | 6/2015 | Vishwanathan | A61N 2/004 600/10 |
| 2018/0271949 A1 * | 9/2018 | Struck | A61K 9/0051 |
| 2021/0077821 A1 * | 3/2021 | De Clerck | A61N 2/002 |

FOREIGN PATENT DOCUMENTS

| | | | | |
|---|---|---|---|---|
| EP | 1036574 A1 * | 9/2000 | | A61F 7/00 |
| GB | 2557900 A | 7/2018 | | |
| JP | H06-63162 A | 3/1994 | | |
| JP | 2000-225176 A | 8/2000 | | |
| KR | 20110052355 A * | 5/2011 | | A61L 2/04 |
| WO | WO-2018/013935 A1 | 1/2018 | | |
| WO | WO-2018/034983 A2 | 2/2018 | | |

OTHER PUBLICATIONS

International Search Report from corresponding PCT Application No. PCT/NL2019/050649, dated Mar. 20, 2020.
International Preliminary Report on Patentability from corresponding PCT Application No. PCT/NL2019/050649, dated Mar. 23, 2021.
Non-Final Office Action from Corresponding Japanese Application No. 2021-516961, Dated Jul. 10, 2023.
Office Action from corresponding Japanese Patent Application No. 2021-516961, Apr. 10, 2024.

* cited by examiner

HEATING APPARATUS AND METHODS

CROSS-REFERENCE TO RELATED APPLICATIONS

This application is a national phase application of PCT Application No. PCT/NL2019/050649, filed on 26 Sep. 2019, which claims priority to Netherland Patent Application Nos. 2021715, filed on 26 Sep. 2018 and U.S. Pat. No. 2,021,722, filed on 27 Sep. 2018. The entire disclosure of the applications identified in this paragraph is incorporated herein by references.

FIELD OF THE INVENTION

The present invention relates to an apparatus for heating. In particular, but not exclusively, the present invention relates to apparatus and methods for the inductive heating of prosthetics or implants, or at least portions thereof, such as for treating biofilm infections of metal implants.

BACKGROUND TO THE INVENTION

Infection of implants is a major problem in elective and trauma surgery. A considerable proportion of prosthetic implants and an even greater proportion of implants in fractures become infected.

Such infections can trigger an immune response that can at least help counter the infection, particularly in combination with antibiotics and/or other drugs. However, especially where an undesirable biofilm develops at or on the prosthetic, treatment is often by invasive surgery. The infected area is opened up, cleansed and treated. To eradicate the infection effectively, it may be necessary to keep the wound open for some considerable time, often causing discomfort to the patient. Some prior art procedures disclose heating of limbs or patients comprising implants, however requiring very high field strengths, and likely leading to internal burns due to the difficult control of the heat deployment.

For example, where a hip prosthetic is associated with an infection, an existing (or new) wound is opened up to access the hip prosthetic. The hip prosthetic is exposed to allow thorough cleansing of the prosthetic and surrounding tissue to try to eradicate the infection. In some cases, the infection may necessitate the removal of the prosthetic, such as for replacement by a new prosthetic.

US-A-2011/251687 discloses a small coil implement to heat small oral shape memory material implant by induction for a period of less than 5 seconds, to return it to its original shape after introduction into a human ear. However, the size of the coil does not permit to generate a field strong enough to heat an implant or prosthetic to reduce a biofilm on a surface thereof, as exemplified in the data relating to the eddy current penetration depth in Nitinol summarised herein. WO2018/013935 discloses a method and apparatus for heating implants, by submitting the entire body of patient to a magnetic field. While this method can heat an implant, the control of the field and energy supplied is difficult to dose or concentrate at a specific area, resulting in enhanced tissue damage possibly leading to loss of fixation and subsequent revision surgery. Also, in presence of an infection, the heat generated may be dissipated quickly by surrounding liquids, and hence renders the disclosed method unsuitable.

It may be an object of one or more aspects, examples, embodiments or claims of the present disclosure to solve or at least mitigate one or more of the problems of the prior art, such as herein described or otherwise.

SUMMARY

According to a first aspect there is provided an apparatus for heating at least a portion of a prosthetic or implant.

The apparatus may comprise an induction heating apparatus for the inductive heating of the portion of the prosthetic or implant.

The portion of the prosthetic or implant may be heatable by induction. The portion of the prosthetic or implant may be directly heatable by induction.

The apparatus may comprise a coil, the coil being configured to inductively heat the portion of the prosthetic or implant. The coil may be configured to inductively heat only the portion of the prosthetic or implant. The apparatus may comprise an induction coil. The apparatus may comprise at least one external induction coil. The external induction coil may be external to a body and/or housing of the apparatus. The induction coil may be configured for direct application to the portion of the prosthetic or implant. In at least some examples, the induction coil may be configured to directly contact the prosthetic or implant. The apparatus may be configured to transmit energy to the portion of the prosthetic or implant without the energy first passing through a patient's skin. The coil may be sized and dimensioned to be smaller than a body portion associated with the prosthetic or implant. For example, the coil may comprise a smaller diameter and/or longitudinal extent than a limb associated with the prosthetic or implant (e.g. the coil may comprise a smaller diameter than a diameter of a patient's leg). The apparatus may be configured to position the portion of the prosthetic or implant within a distance from or of the coil, the distance being less than or equal to a dimension of the coil. For example the apparatus may be configured to position the coil closer to the portion of the prosthetic or implant than a diameter of the coil. The coil may be configured for insertion into or through a surgical incision.

The prosthetic or implant may comprise a conductive material. The portion of the prosthetic or implant may comprise the conductive material. The prosthetic or implant may comprise a metal. The prosthetic or implant may comprise one or more of: steel; titanium; an alloy/s; cobalt-chromium. The conductive material may be inductively heatable.

The apparatus may comprise a handheld apparatus. The apparatus may comprise a single-handed apparatus. The apparatus may be configured for single-handed use by a user. The apparatus may comprise a pistol apparatus. The apparatus may comprise a handle for gripping by a single hand. The single hand may be a left hand or a right hand or either one of a left or right hand. The handle may comprise a pistol grip handle. The apparatus may be configured for control by the gripping hand. The apparatus may comprise an actuator for operation by the gripping hand. The actuator may comprise a trigger. The actuator may be for at least partially controlling an administration of heat by the apparatus, such as by controlling a power, such as an amount and/or duration of power, supplied to the induction coil.

The apparatus may comprise a portable apparatus. The apparatus may comprise a low-powered apparatus. The apparatus may comprise a low voltage apparatus. The voltage may be less than or equal to about 60 volts. In at least some examples, the voltage may be less than or equal to about 50 volts; less than or equal to about 30 volts; less than or equal to about 20 volts; or equal to about 12 volts. The apparatus may be configured to provide an operating frequency of a Pulsed Electromagnetic Field (PEMF) of less than about 100 kHz. The apparatus may comprise a battery-powered apparatus. Additionally, or alternatively, the apparatus may comprise a mains or grid-powered apparatus, such as with or for power via a cable and plug.

The apparatus may be configured to treat infection. The apparatus may comprise an infection treatment apparatus. The apparatus may be configured to at least assist in killing bacteria. The apparatus may be configured to heat bacteria to a critical temperature whereby bacteria are at least weakened, such as to assist in infection control by other means such as administered drugs and/or immuno-defence mechanisms. The apparatus may be configured to administer heat to a biofilm associated with the prosthetic or implant.

The portion of the prosthetic or implant comprises at least one boundary or surface configured to engage or interact or interface with tissue, such as muscle and/or bone and/or cartilage tissue.

The term "prosthetic or implant" herein may relate to orthopaedic implants such as for instance a total joint replacement, a total or hemi-joint arthroplasty; a total joint prosthesis; a joint replacement; e.g. a hip prosthetic; a joint replacement implant; joint prosthesis; joint reconstruction prosthesis; a joint reconstruction implant; a fracture fixation device, including but not limited to plate, screws, nails, staple, rods, wire, pins, external fixators; a joint distraction device, i.e. an external fixator. Preferably, the term "prosthetic or implant" refers to a loaded or loadable implant. As an example, during joint replacement surgery, also referred to as replacement arthroplasty, a joint implant is inserted into or otherwise attached to a bone that has been prepared to receive the implant, and the implant is secured to achieve a reliable stabilization, or fixation, for bearing loads. Accordingly, the term "prosthetic implant" herein preferably refers to a (partial) metal device with biomechanical function(s) implanted near, to or in a bone.

The term "invasive species" may relate to certain invasive microorganisms, in particular bacteria, to form colonies, and eventually a biofilm. A biofilm typically comprises a conglomerate of microbial organisms embedded in a highly hydrated matrix of exopolymers, typically polysaccharides and/or other macromolecules. Biofilms may contain either single or multiple microbial species and readily adhere to surfaces of prosthetics and/or implants. Prevention of colonization by, and eradication of biofilm-associated microorganisms is often difficult, as the structural matrix established during biofilm formation usually allows the colonizing cells to withstand normal treatment doses of antibiotics, as the glycocalyx matrix appears to serve as a barrier protecting and isolating the microorganisms from host defence mechanisms such as antibodies and phagocytes as well as from antimicrobial agents including surfactants, biocides and antibiotics. Once established, a biofilm itself may be refractory to treatment, providing, in effect, a reservoir of infection which can lead to recurrence of the infection after an antibiotic treatment. Biofilm infection is often associated with septic arthritis, where biofilm formation on joint or implant surfaces can lead to a chronic and recurrent infection. In addition to sepsis, the biofilm infection can cause destruction of the joint surface material, in particular in implants, such as bone prostheses and the like, thereby necessitating additional surgery or surgeries, commonly referred to as corrective or revision surgeries to remove the infectious material, as well as necrotic or infected tissue.

The term "active count" herein relates to a measurement for the determination of active or viable invasive microorganisms in or derived from a biofilm after the treatment. This may for instance be done by a probe active count assay (PAC), or by a different cell count method or protocol.

The apparatus may be configured to heat the boundary or surface. The apparatus may be configured to directly and/or indirectly heat the boundary or surface. In at least some examples the boundary or surface comprises the conductive material. In at least some examples the boundary or surface comprises a non or less conductive material, the non or less conductive material being associated with the conductive material. For example, the prosthetic or implant may comprise a non or less conductive coating or layer, the apparatus being configured to indirectly heat the coating or layer by inducing heat in the associated conductive material, such as underlying the coating or layer, with the heat being transmitted or propagated from the conductive material to or through the non or less conductive material, such as by conduction.

Additionally, or alternatively, the apparatus may be configured to heat the at least a portion of the prosthetic or implant to assist in attaching and/or detaching the prosthetic or implant. For example the apparatus may be configured to heat the portion of the prosthetic or implant to expand the portion of the prosthetic or implant. In at least some examples, the portion of the prosthetic or implant to be heated may be associated with a fixation of the prosthetic or implant. For example, the portion of the prosthetic or implant may comprise a socket or recess. The socket or recess may be associated with another portion of the prosthetic or implant, such as for receiving another part or component of the prosthetic or implant. For example, where the prosthetic or implant comprises a fixture or fastening for securement, the apparatus may be configured to heat the fitting or securement, or at least a portion thereof, to assist in application and/or removal of the prosthetic or implant. The apparatus may be configured to thermally expand and/or contract the portion of the prosthetic or implant. In at least some examples, the apparatus may be configured to sequentially and/or cyclically thermally expand and contract the portion of the prosthetic or implant.

The apparatus may be configured to weaken a fastening for or of the prosthetic or implant, such as for assistance in temporary or permanent removal of the portion of the prosthetic or implant. For example, where a prosthetic or implant has been secured, such as directly or indirectly to a bone, the apparatus may be configured to weaken an interface between the prosthetic or implant and the bone. The apparatus may be configured to weaken a bond, such as with a bonding means or agent, between the prosthetic or implant and the patient.

The apparatus may be configured to heat the portion of the prosthetic of implant in vitro prior to insertion or application of the portion of the prosthetic or implant to the patient. Additionally or alternatively, the apparatus may be configured to heat the portion of the prosthetic or implant in vivo, whilst the portion of the prosthetic or implant is attached to, or located in, the patient.

In at least some examples, the apparatus may be configured to heat the portion of prosthetic or implant during a surgical procedure. The surgical procedure may comprise an invasive surgical procedure. Alternatively, the surgical procedure may comprise a non-invasive surgical procedure.

The apparatus may be configured for in vivo use. The apparatus may be configured to heat the portion of the prosthetic or implant whilst the portion of the prosthetic or implant is located in and/or attached to a body. Additionally or alternatively, the apparatus may be configured for ex vivo use. The apparatus may be configured for in vitro use. The apparatus may be configured to heat the portion of the prosthetic or implant whilst the portion of the prosthetic or implant is located outside and/or detached from the body. In at least some examples, the apparatus may be configured to heat the portion of the prosthetic or implant ex vivo during a surgical procedure, such as where the prosthetic or implant (or portion thereof) is detached and/or removed from the body.

The apparatus may be configured to heat the portion of the prosthetic or implant during the surgical procedure without unduly heating patient tissue. The apparatus may be configured to heat the portion of the prosthetic or implant to a temperature at or below a maximum temperature. The maximum temperature may be associated with tissue damage. For example, the apparatus may be configured to heat the portion of the prosthetic or implant only to temperatures unassociated with undesirable tissue damage.

The apparatus may be configured to heat the portion of the prosthetic or implant to a temperature at or below a minimum temperature. The minimum temperature may be associated with infection control. For example, the minimum temperature may be associated with killing, or at least combatting, infection.

In at least some examples, the minimum temperature may be, at least 38° C.; at least 40° C.; at least 50° C.; at least 60° C.; at least 65° C.; at least 70° C.; or at least 75° C.; or at least 80° C.; or at least 90° C. The maximum temperature may be at least 60° C.; at least 65° C.; at least 70° C.; at least 75° C.; or at least 80° C.; or at least 90° C.; or at least 100° C.; or at least 110° C. or at least 120° C. Accordingly, in at least some examples, the apparatus may be configured to heat the portion of the prosthetic or implant to a temperature in a range, such as in a range from about 65° C. to about 70° C. Preferably, the portion of the prosthetic or implant to a temperature from about 60° C. to about 90° C., in particular of from 65° C. to 70° C., preferably for a period suitable to reduce the active count of invasive cell species forming a biofilm.

The apparatus may be configured to heat the portion of the prosthetic or implant to a target temperature. The apparatus may be controlled in dependence of a temperature of the portion of the prosthetic or implant, and/or additional temperature/s, such as of other portion/s of the prosthetic or implant and/or tissue (e.g. bone, muscle, cartilage, nerves, etc). The apparatus may be controllable in dependence on a thermal sensor or thermometer. In at least some examples, the apparatus may be controllable in dependence on a direct temperature measurement/s. The apparatus may be configured to operate with a temperature measurement device. The temperature measurement device may comprise a sensor/s and/or a camera/s. The camera may comprise an infra red thermal camera. The temperature measurement device may comprise an augmented and/or a virtual reality device. The apparatus may be configured to adapt the heating, such as via the power output to or from the coil, in dependence on the temperature measurement device. The apparatus may be configured to automatically adapt the heating. For example, the apparatus may comprise, or at least be in data communication with, the temperature measurement device. Additionally, or alternatively, the apparatus may be configured to manually adapt the heating. For example, an operator or user of the device may manually adapt the heating with the apparatus in dependence on information the operator or user receives from the temperature measurement device. The apparatus may be operated in dependence of real time visualisation and/or measurement, such as with a display connected to or provided by an infra-red thermal camera. The apparatus may be configured to adapt the heating in dependence on a cumulative thermal dose. The temperature measurement device, or associated device, may be configured to calculate the cumulative thermal dose real time. The temperature measurement device, or associated device, may be configured to display the temperature/s and/or cumulative thermal dose/s to the user or operator, such as a surgeon. In at least some examples, the apparatus may integrally comprise a thermal sensor and a (micro-)controller.

The apparatus may be configured to heat only a portion of the prosthetic or implant. For example, the apparatus may be configured to not heat the entire prosthetic or implant. The apparatus may be configured to induce heat in only a single portion of the prosthetic or implant at a time. The apparatus may be configured to not heat the entire prosthetic or implant simultaneously.

The apparatus may be configured to selectively heat the portion of the prosthetic or implant. The apparatus may be configured to selectively heat only part of the implant that is safe. The apparatus may be configured to selectively heat only part of the implant that is no or low-risk. The apparatus may be configured to avoid heating areas of the implant associated with bone fixation (e.g. for total joint replacements); and/or areas of the prosthetic or implant in proximity to or associated with important anatomical structures such as nerves (e.g. in case of infected plate in elbow). Alternatively, high risk areas (e.g. for loss of bone fixation or proximity of nerves/vessels) may be heated at or to a lower temperature/s (e.g. relative to low risk areas). The coil may be a precision coil for targeting only the portion of the prosthetic or implant to be heated.

The apparatus may be configured to inductively heat a first portion of the prosthetic or implant, whilst not inductively heating a second portion of the prosthetic or implant. The apparatus may be configured to allow heat transfer from the first portion of the prosthetic or implant to the second portion of the prosthetic or implant. The apparatus may be configured to utilise the second portion of the prosthetic or implant as a heat sink for the first portion of the prosthetic or implant. Additionally or alternatively, the apparatus may comprise a cooling system. The cooling system may comprise an active cooling system. The cooling system may be for cooling the coil.

The apparatus may be configured to sequentially heat two or more portions of the prosthetic or implant, such as by heating a first portion prior to heating a second portion of the prosthetic or implant.

In at least some examples, the at least a portion of the prosthetic or implant comprises the entire prosthetic or implant.

The apparatus may be configured for sterilisation. The apparatus may be configured for sterilisation using a sterilisation device for sterilising surgical equipment, such as standard sterilising device for sterilising the likes of a surgical drill, surgical saw or the like. The sterilisation may comprise one or more of: autoclaving; dry heat; chemical sterilant/s; mechanical and/or ultrasonic cleaning. The apparatus may be sized and dimensioned for location in a conventional or standard sterilisation means, such as for the likes of a surgical drill, surgical saw or the like.

The apparatus may comprise one or more disposable components. For example, the apparatus may comprise one or more battery cells. In at least some examples, the battery cell/s is/are removed prior to sterilisation. A new battery cell/s may be inserted into or provided to the apparatus for a subsequent use of the apparatus, post-sterilisation. The apparatus may comprise one or more detachable components. For example, the external coil may be detachable, and optionally re-attachable.

In at least some examples, the coil may be deformable in dependence on the portion of the prosthetic or implant. The deformation may be plastic and/or elastic. The coil may be configured to deform to adapt to the prosthetic or implant. The coil may be configured to be deformed by the prosthetic or implant. The coil may be configured to be deformed by manipulation by the user. For example, the user may plastically and/or elastically deform the coil to adapt to a shape of a particular prosthetic or implant.

The prosthetic or implant may comprise a prosthetic or implant for implantation into and/or attachment to a human body. Alternatively, the prosthetic or implant may comprise a prosthetic or implant for implantation into and/or attachment to a non-human body, such as a non-human mammal.

According to a further aspect there is provided a system or assembly for heating at least a portion of a prosthetic or implant. The system or assembly may comprise an apparatus and at least a portion of a prosthetic or implant. The apparatus may comprise the apparatus of any other aspect, claim, example or embodiment. The at least a portion of a prosthetic or implant may comprise the at least a portion of a prosthetic or implant of any other aspect, claim, example or embodiment. The apparatus may be configured in dependence on the at least a portion of a prosthetic or implant. For example, the apparatus may comprise a coil and/or power supply configured for a property of the at least a portion of a prosthetic or implant. The system or assembly may comprise an array of coils, such as interchangeable and/or disposable coils. The system or assembly may comprise a temperature control mechanism. The temperature control mechanism may be that of any other aspect, example, claim or embodiment. The temperature control mechanism may be part of or incorporated into or linked to the heating apparatus. Alternatively, the temperature control mechanism may be at least partially discrete from the heating apparatus. The temperature control mechanism may comprise a temperature sensor or measurement device. The temperature measurement device may be that of any other aspect, claim, embodiment, or example.

According to a further aspect there is provided a method of heating at least a portion of a prosthetic or implant.

The method may comprise in vitro heating. The method may comprise ex vivo heating. Additionally, or alternatively, the method may comprise in vivo heating.

The method may comprise an induction heating method for the inductive heating of the portion of the prosthetic or implant.

The method may comprise directly heating the portion of the prosthetic or implant by induction.

In one aspect, the present invention also relates to a method of reducing the active count of microorganisms which form a biofilm on a surface expanse of a prosthetic or implant. In another aspect, the present invention also provides a method of potentiating the action of antibiotic compositions in reducing biofilms refractory to antibiotic effects when the antibiotic in absence of the treatment may not be able to attack the biofilm in absence of the heat treatment. In a typical embodiment, the biofilm is composed predominantly of bacteria, and the biocide comprises an antibiotic, such as one of the penicillins, cephalosporins, aminoglycosides, tetracyclines, sulfonamides, and quinolones. Alternatively, the biocide may comprise compounds useful for sterilisation, e.g. chlorhexidine. Also forming part of the invention is a method of potentiating the effect of an antibiotic composition in reducing the active count of microorganisms which form a biofilm on a surface expanse of a prosthetic or implant, wherein the effect of the antibiotic is potentiated by heat treatment of the prosthetic or implant, wherein the biofilm microorganisms are attacked from the interior surface expanse of the biofilm, in the presence of the antibiotic, wherein the concentration of the antibiotic is less than that effective to reduce the biofilm microorganisms in the absence of the heat treatment.

The method may comprise configuring a coil to inductively heat the portion of the prosthetic or implant. The method may comprise inductively heating only the portion of the prosthetic or implant. The method may comprise induction heating with an external induction coil, external to a body and/or housing of a heating apparatus, such as the heating apparatus of any other aspect, embodiment, example or claim. The method may comprise configuring the coil for direct application to the portion of the prosthetic or implant. The method may comprise directly applying the coil to the portion of the prosthetic or implant. The method may comprise directly contacting the prosthetic or implant with the coil. The method may comprise transmitting energy to the portion of the prosthetic or implant without the energy first passing through a patient's skin. The method may comprise avoiding or at least minimising passage of energy through a patient's skin and/or tissue. The method may comprise positioning the portion of the prosthetic or implant within a distance from or of the coil, the distance being less than or equal to a dimension of the coil. The method may comprise positioning the coil and/or the portion of the prosthetic or implant. For example the method may comprise positioning the coil closer to the portion of the prosthetic or implant than a diameter of the coil. The method may comprise inserting the coil into or through a surgical incision.

The method may comprise providing the heat via a handheld apparatus. The method may comprise at least partially controlling an administration of heat, such as by controlling a power, such as an amount and/or duration of power, supplied to the induction coil.

The method may comprise providing an operating frequency of a Pulsed Electromagnetic Field (PEMF) of less than about 100 kHz.

The method may comprise treating an infection, such as a prosthetic joint infection (PJI). The method may comprise an infection treatment method. The method may comprise at least assisting in killing invasive species, such as bacteria. The method may comprise heating the invasive species, in particular bacteria, to a critical temperature whereby bacteria are at least weakened, such as to assist in infection control by other means such as administered drugs and/or immuno-defence mechanisms. The method may comprise administering heat to a biofilm associated with the prosthetic or implant.

The method may comprise heating at least one boundary or surface configured to engage or interact or interface with tissue, such as muscle and/or bone and/or cartilage tissue, and the like. The method may comprise heating the boundary or surface. The method may comprise directly and/or indirectly heating the boundary or surface. In at least some examples the boundary or surface comprises a non or less conductive material, the non or less conductive material being associated with the conductive material. For example, the prosthetic or implant may comprise a non or less conductive coating or layer, the method comprising indirectly heating the coating or layer. The method may comprise inducing heat in the associated conductive material, such as underlying the coating or layer, with the heat being transmitted or propagated from the conductive material to or through the non or less conductive material, such as by conduction.

Additionally, or alternatively, the method may comprise heating the at least a portion of the prosthetic or implant to assist in attaching and/or detaching the prosthetic or implant. For example the method may comprise heating the portion of the prosthetic or implant to expand the portion of the prosthetic or implant. In at least some examples, the portion of the prosthetic or implant to be heated may be associated with a fixation of the prosthetic or implant. For example, the portion of the prosthetic or implant may comprise a socket or recess. The socket or recess may be associated with another portion of the prosthetic or implant, such as for receiving another part or component of the prosthetic or implant. For example, where the prosthetic or implant comprises a fixture or fastening for securement, the method may comprise heating the fitting or securement, or at least a portion thereof, to assist in application and/or removal of the prosthetic or implant. The method may comprise thermally expanding and/or contracting the portion of the prosthetic or implant. The method may comprise heating the portion of the prosthetic or implant prior to and/or during attachment, connection or insertion of the portion of the prosthetic or implant. The method may comprise heating to ease attachment, connection or insertion, such as by thermally adapting clearances or tolerances to provide for a looser fit during attachment, connection or insertion. The method may comprise subsequent cooling, such as passive cooling, to thermally adapt clearances or tolerances to provide for a tighter fit when attached, connected or inserted. The method may comprise heating the portion of the prosthetic or implant during temporary or permanent removal or loosening of the prosthetic or implant, such as during an invasive procedure. The method may comprise heating the portion of the prosthetic or implant to loosen the prosthetic or implant. In at least some examples, the method may comprise sequentially and/or cyclically thermally expanding and contracting the portion of the prosthetic or implant.

The method may comprise weakening a fastening for or of the prosthetic or implant, such as for assisting in the temporary or permanent removal of the portion of the prosthetic or implant. For example, where a prosthetic or implant has been secured, such as directly or indirectly to a bone, the method may comprise weakening an interface between the prosthetic or implant and the bone. The method may comprise weakening a bond, such as with a bonding means or agent, between the prosthetic or implant and the patient.

The method may comprise heating the portion of the prosthetic of implant in vitro prior to insertion or application of the portion of the prosthetic or implant to the patient. Additionally or alternatively, the method may comprise heating the portion of the prosthetic or implant in vivo, whilst the portion of the prosthetic or implant is attached to, or located in, the patient—or being attached to, or being located in the patient.

In at least some examples, the method may comprise heating the portion of prosthetic or implant during a surgical procedure. The method may comprise an invasive surgical procedure. Alternatively, the method may comprise a non-invasive procedure. The method may comprise a treatment of the prosthetic or implant, but not a treatment of the patient as such.

The method may comprise in vivo use. The method may comprise heating the portion of the prosthetic or implant whilst the portion of the prosthetic or implant is located in and/or attached to a body. Additionally or alternatively, the method may comprise ex vivo use. The method may comprise in vitro use. The method may comprise heating the portion of the prosthetic or implant whilst the portion of the prosthetic or implant is located outside and/or detached from the body. In at least some examples, the method may comprise heating the portion of the prosthetic or implant ex vivo during a surgical procedure, such as where the prosthetic or implant (or portion thereof) is detached and/or removed from the body.

The method may comprise heating the portion of the prosthetic or implant during the surgical procedure without unduly heating patient tissue. The method may comprise heating the portion of the prosthetic or implant to a temperature at or below a maximum temperature. The maximum temperature may be associated with tissue damage. For example, the method may comprise heating the portion of the prosthetic or implant only to temperatures unassociated with undesirable tissue damage. The method may comprise preventing or at least minimising tissue damage.

The method may comprise heating the portion of the prosthetic or implant to a temperature at or below a minimum temperature. The minimum temperature may be associated with infection control. For example, the minimum temperature may be associated with killing, or at least combatting, infection. The method may comprise heating the portion of the prosthetic or implant to a temperature in a range, such as in a range from about 65° C. to about 700.

The method may comprise heating the portion of the prosthetic or implant to a target temperature. The method may comprise controlling heating in dependence of a temperature of the portion of the prosthetic or implant, and/or additional temperature/s, such as of other portion's of the prosthetic or implant and/or tissue (e.g. bone, muscle, cartilage, nerves, etc). The method may comprise controlling heating in dependence on a thermal sensor or thermometer. The method may comprise direct temperature measurement's. The method may comprise operating a temperature measurement device. The method may comprise providing an augmented and/or a virtual reality. The method may comprise adapting the heating, such as via the power output to or from the coil, in dependence on the temperature measurement device. The method may comprise automatically adapting the heating. Additionally, or alternatively, the method may comprise manually adapting the heating. For example, the method may comprise an operator or user of the device manually adapting the heating in dependence on information the operator or user receives from the temperature measurement device. The method may comprise real time visualisation and/or measurement, such as provided by a display connected to or associated with an infra-red thermal camera. The method may comprise adapting the heating in dependence on a cumulative thermal dose. The method may comprise calculating the cumulative thermal dose real time. The method may comprise displaying the temperature/s and/or cumulative thermal dose's to the user or operator, such as a surgeon. In at least some examples, the method may comprise automatically adapting the heating with an integral thermal sensor and a (micro-)controller comprised in the heating apparatus.

The method may comprise heating only a portion of the prosthetic or implant. For example, the method may comprise not heating the entire prosthetic or implant. The method may comprise inducing heat in only a single portion of the prosthetic or implant at a time. The method may comprise not heating the entire prosthetic or implant simultaneously.

The method may comprise selectively heating the portion of the prosthetic or implant. The method may comprise selectively heating only part of the implant that is safe. The method may comprise selectively heating only part of the implant that is no or low-risk. The method may comprise avoiding heating areas of the implant associated with bone fixation (e.g. for total joint replacements); and/or areas of the prosthetic or implant in proximity to or associated with important anatomical structures such as nerves (e.g. in case of infected plate in elbow). Alternatively, high risk areas (e.g. for loss of bone fixation or proximity of nerves/vessels) may be heated at or to a lower temperature's (e.g. relative to low risk areas). The method may comprise targeting only the portion of the prosthetic or implant to be heated, such as with a precision coil.

The method may comprise inductively heating a first portion of the prosthetic or implant, whilst not inductively heating a second portion of the prosthetic or implant. The method may comprise allowing heat transfer from the first portion of the prosthetic or implant to the second portion of the prosthetic or implant. The method may comprise utilising the second portion of the prosthetic or implant as a heat sink for the first portion of the prosthetic or implant. Additionally or alternatively, the method may comprise cooling, such as actively cooling, the coil; and/or the portion of the prosthetic and/or other portion/s of the prosthetic or implant; and/or patient tissue.

The method may comprise sequentially heating two or more portions of the prosthetic or implant, such as by heating a first portion prior to heating a second portion of the prosthetic or implant.

In at least some examples, the method comprises heating the entire prosthetic or implant.

The method may comprise sterilisation. The method may comprise sterilisation using a sterilisation device for sterilising surgical equipment, such as standard sterilising device for sterilising the likes of a surgical drill, surgical saw or the like. The sterilisation may comprise one or more of: autoclaving; dry heat; chemical sterilant/s; mechanical and/or ultrasonic cleaning.

In at least some examples, the method may comprise deforming the coil in dependence on the portion of the prosthetic or implant. The deformation may be plastic and/or elastic. The method may comprise deforming the coil to adapt to the prosthetic or implant. The method may comprise deforming the coil by the prosthetic or implant, such as by forcing the coil or prosthetic or implant against the other of the coil or prosthetic/implant. The method may comprise deforming the coil by manipulation by the user. For example, the method may comprise the user plastically and/or elastically deforming the coil to adapt to a shape of a particular prosthetic or implant.

The method may comprise heating a prosthetic or implant for implantation into and/or attachment to a human body. Alternatively, the method may comprise heating a prosthetic or implant for implantation into and/or attachment to a non-human body, such as a non-human mammal. The method may comprise implanting and/or attaching the prosthetic or implant. Additionally or alternatively, the method may comprise removing and/or detaching the prosthetic or implant.

The invention may include one or more corresponding aspects, embodiments or features in isolation or in various combinations whether or not specifically stated (including claimed) in that combination or in isolation. For example, it will readily be appreciated that features recited as optional with respect to one aspect, example, embodiment or claim may be additionally applicable with respect to another aspect, example, embodiment or claim, without the need to explicitly and unnecessarily list those various combinations and permutations here (e.g. the apparatus of one aspect may comprise features of any other aspect). Optional features as recited in respect of a method may be additionally applicable to an apparatus or device; and vice versa. For example, an apparatus may be configured to perform a feature of a method of any other aspect, example, embodiment or claim. In addition, corresponding means for performing one or more of the discussed functions are also within the present disclosure.

DESCRIPTION OF THE DRAWINGS

Embodiments of the present invention are described below, by way of example only, with reference to the accompanying drawings, in which.

DETAILED DESCRIPTION

Figure 1:
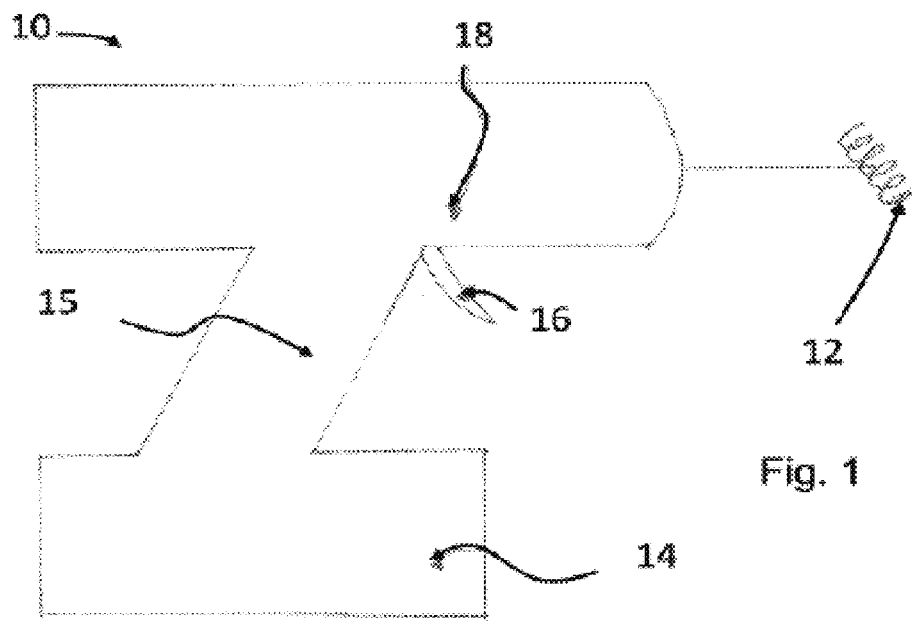
FIG. 1 shows a schematic representation of an apparatus for heating at least a portion of a prosthetic or implant, according to a first example of the present disclosure.

Referring first to FIG. 1, there is shown an apparatus 10 for heating at least a portion of a prosthetic or implant, according to a first example of the present disclosure. Here, the apparatus 10 comprises an induction heating apparatus for the inductive heating of the portion of the prosthetic or implant (not shown in FIG. 1).

Figure 4:
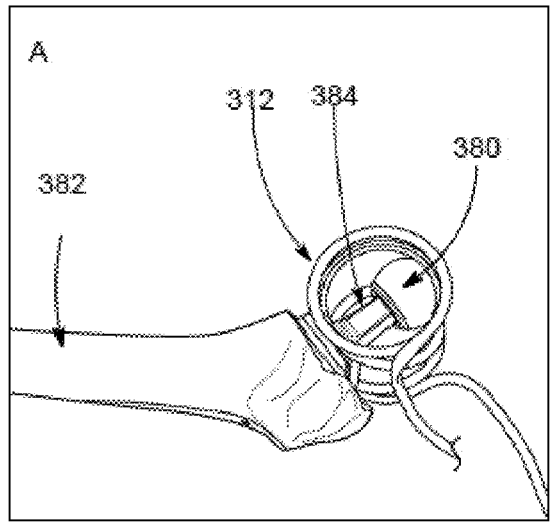
FIGS. 4 to 11 show respective portions of prosthetic implants for heating by the apparatus of FIGS. 1 and/or 2.

The apparatus comprises an external induction coil 12, the coil 12 being configured to inductively heat the portion of the prosthetic or implant. The coil 12 is configured to inductively heat only the portion of the prosthetic or implant. As shown here, the external induction coil 12 is external to a body or housing 18 of the apparatus 10. The induction coil 12 is configured for direct application to the portion of the prosthetic or implant, as shown in FIG. 4 onwards. Here, the induction coil 12 is configured to directly contact the prosthetic or implant. The apparatus 10 is configured to transmit energy to the portion of the prosthetic or implant without the energy first passing through a patient's skin. The coil 12 is sized and dimensioned to be smaller than a body portion associated with the prosthetic or implant. For example, here the coil 12 comprises a smaller diameter and longitudinal extent than a limb associated with the prosthetic or implant (e.g. the coil 12 comprises a smaller diameter than a diameter of a patient's leg). The apparatus 10 is configured to position the portion of the prosthetic or implant within a distance from or of the coil 12, the distance being less than or equal to a dimension of the coil 12. For example, here, the apparatus 10 is configured to position the coil 12 closer to the portion of the prosthetic or implant than a diameter of the coil 12. The coil 12 here is configured for insertion into or through a surgical incision.

The apparatus 10 here comprises a portable handheld pistol apparatus, for single-handed use by a user. The apparatus 10 comprises pistol grip handle 15 for control by a gripping hand, with an actuator 16 for operation by the gripping hand, in the form of a trigger. The actuator 16 is for at least partially controlling an administration of heat by the apparatus 10, such as by controlling a power, such as an amount and/or duration of power, supplied to the induction coil 12.

As shown in FIG. 1, the apparatus 10 comprises a low-powered, low voltage apparatus. Such an apparatus may provide safety, access and/or maintenance benefits. For example, a low voltage apparatus may be safer, particularly for use in a surgical procedure, than a mains or grid-powered apparatus. Here, the voltage can be varied between about 12 volts and about 60 volts, depending on specific requirements. For example, where a larger portion of a prosthetic or implant is to be heated, a larger battery may be fitted in the apparatus 10, in the internal battery compartment 14. The apparatus 10 is configured to provide an operating frequency of a Pulsed Electromagnetic Field (PEMF) of less than about 100 kHz.

Figure 2:
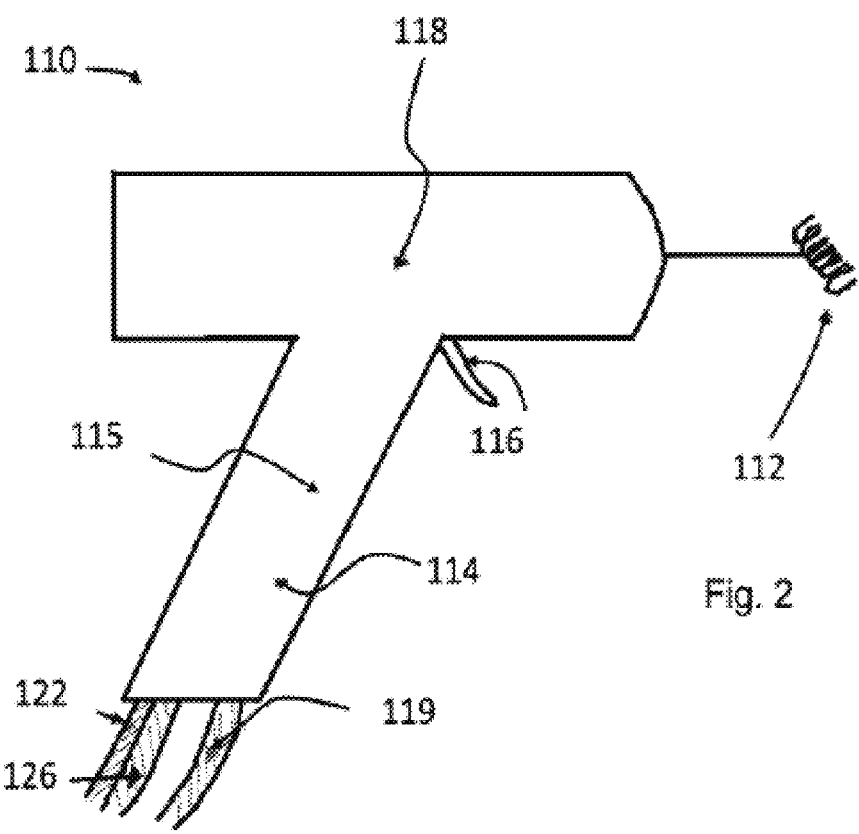
FIG. 2 shows an apparatus for heating at least a portion of a prosthetic or implant, according to a second example of the present disclosure.

Referring now to FIG. 2, there is shown an apparatus 110 for heating at least a portion of a prosthetic or implant, according to a second example of the present disclosure. The apparatus 110 shown in FIG. 2 is generally similar to the apparatus 10 shown in FIG. 1, with similar features denoted by similar references numerals, incremented by 100. Accordingly, the apparatus 110 in FIG. 2 comprises an external induction coil 112 and a pistol grip handle 115. As shown in FIG. 2, the apparatus 110 comprises a mains or grid-powered apparatus, such as with or for power via a cable 119 and plug. It will be appreciated that the mains or grid power supply via the cable 119 may be optional, in that the apparatus 110 of FIG. 2 may be additionally or alternatively powered via an internal battery power source.

As shown in FIG. 2, the apparatus 110 comprises an active cooling system, with an inflow supply 122 and an outflow supply 126 supplying coolant respectively to and from the coil 112. The coolant may be water, such as supplied from a tap source (not shown).

The apparatus 10, 110 shown in FIGS. 1 and 2 is configured for sterilisation using a sterilisation device for sterilising surgical equipment, such as standard sterilising device for sterilising the likes of a surgical drill, surgical saw or the like. The sterilisation comprises one or more of: autoclaving; dry heat; chemical sterilant/s; mechanical and/or ultrasonic cleaning. The apparatus 10, 110 is sized and dimensioned for location in a conventional or standard sterilisation means, such as for the likes of a surgical drill, surgical saw or the like.

Figure 3:
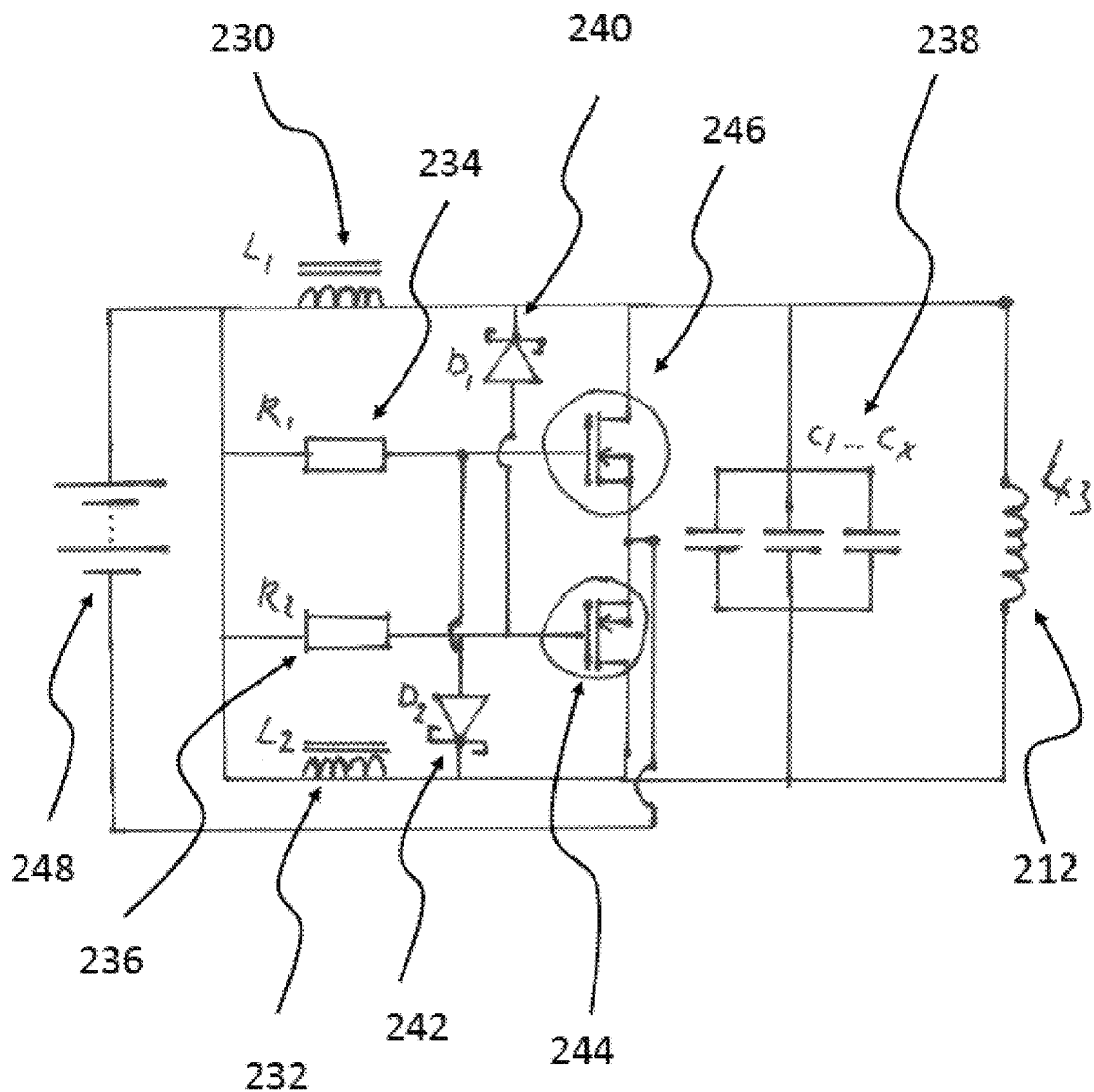
FIG. 3 shows a schematic diagram of an electronic system for the apparatus of FIGS. 1 and/or 2.

Referring now to FIG. 3, there is shown an example of a schematic diagram 200 of an electronic system for the apparatus 10, 110 of FIGS. 1 and/or 2. Accordingly, the exemplary apparatus 10, 110 comprises two internal inductors 230, 232, each being greater than 75 microHenries and greater than 10 A. The external coil 212 corresponds to the coil 12, 112 shown in FIGS. 1 and 2. The pair of resistors shown, 234, 236 are less than 600 Ohms, with specific values depending on a capacitor bank 238 and the configuration of the external coil 212. The capacitor bank 238 has a total capacitance less than 10 microFarad that is dependent on the configuration of the external coil 212. Each of the Schottky diodes 240, 242 is rated greater than 60V and 10 A. The power MOSFETs 244, 246 (metal-oxide-semiconductor field-effect transistors) are greater than 200 W, with $U_{br\ dss}$ greater than 200V. The batteries 248 are between 12V and 60V, selected in dependence on the configuration of the external coil 212.

Referring now to FIGS. 4 to 11, there is shown a plurality of configurations of coils sequentially numbered from 312 to 1012, in increments of 100 for ease of reference. Although indicated with discrete reference numerals for ease of reference, it will be appreciated that a single coil may be shown in multiple figures, such as where the coil is deformable into more than one of the illustrated configurations. Likewise, it will be appreciated that one or more of the coils 312 to 1012 may be for the apparatus of FIGS. 1 and/or 2.

Figure 5:
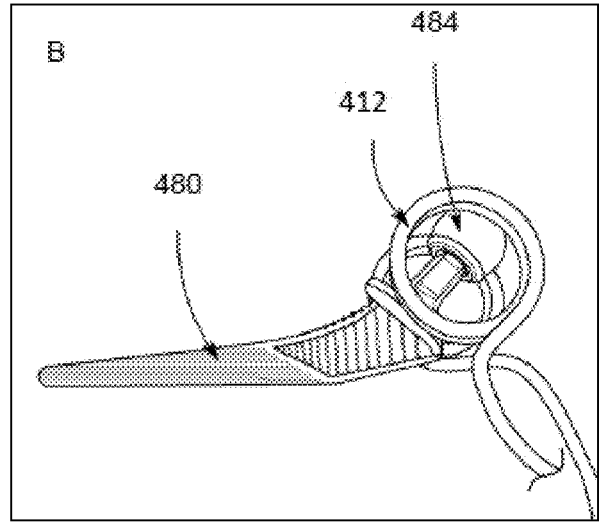
Figure 6:
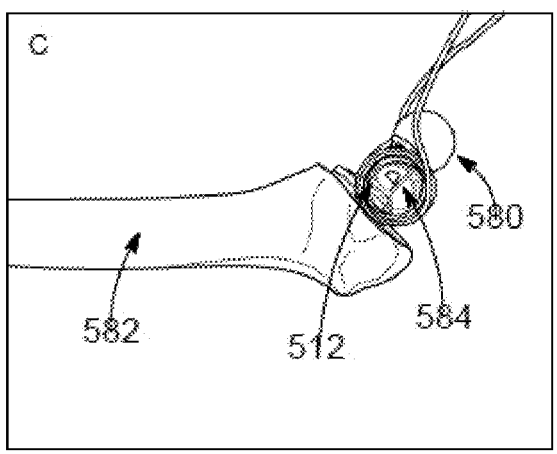

FIGS. 4 to 11 also show respective portions of prosthetic implants 380 to 1080, with FIGS. 4 and 6 showing the prosthetic implants 380, 580 in situ in a bone 382, 582. Where the prosthetic implant 380, 480, 580, 680, 780, 880, 980, 1080 is shown ex vivo (particularly when disconnected from a bone 382, 582), it will be appreciated that the prosthetic implant 380, 480, 580, 680, 780, 880, 980, 1080 can be treated ex vivo, in vitro, such as prior to insertion or reinsertion into a patient (not shown). It will also be appreciated, that in other examples, a similar arrangement of the coils 312 to 1012 and prosthetic implants 380 to 1080 may be located in vivo in patients (not shown).

Figure 12:
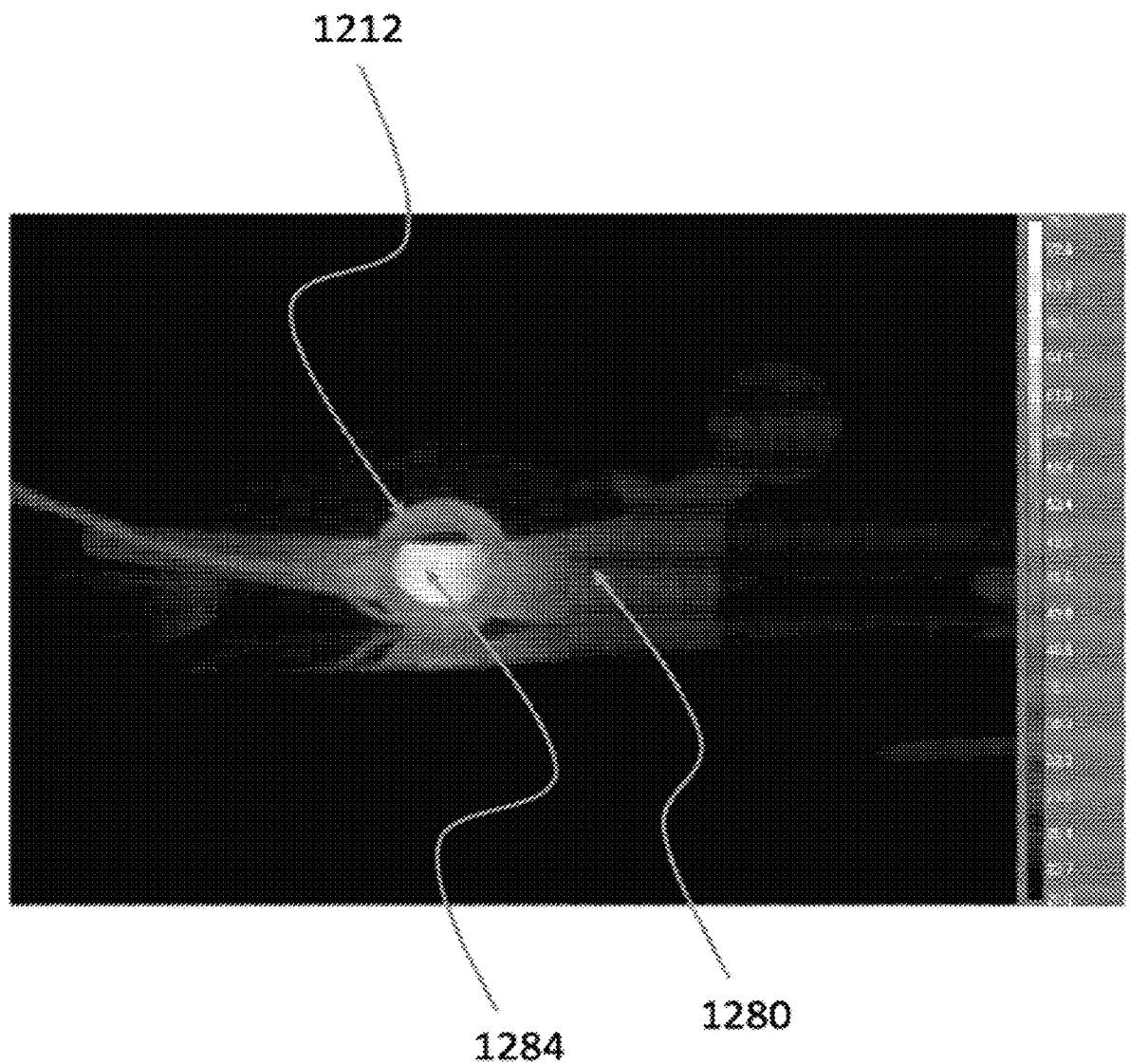
FIG. 12 shows a thermal image indicative of selective heating of an example portion of the prosthetic implant by the apparatus of FIGS. 1 and/or 2.

FIG. 4 shows the prosthetic implant 380 in the form of a metal implant (hip stem) in bone 382 and water cooled hollow coil 312, which coil 312 can heat the metal implant selectively (e.g. see FIG. 12).

FIG. 5 shows the prosthetic implant 480 in the form of a metal implant (hip stem) similar to FIG. 4 with the bone removed.

FIG. 6 shows the prosthetic implant 580 in the form of a metal implant (hip stem) in bone 582 and a "spring coil" 512, which coil 512 can heat the metal implant selectively.

Figure 7:
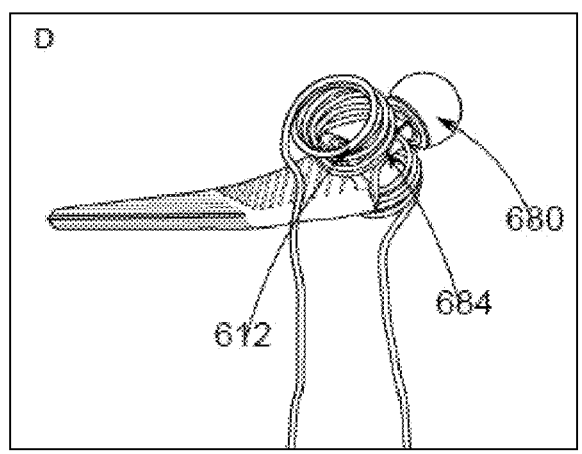
Figure 8:
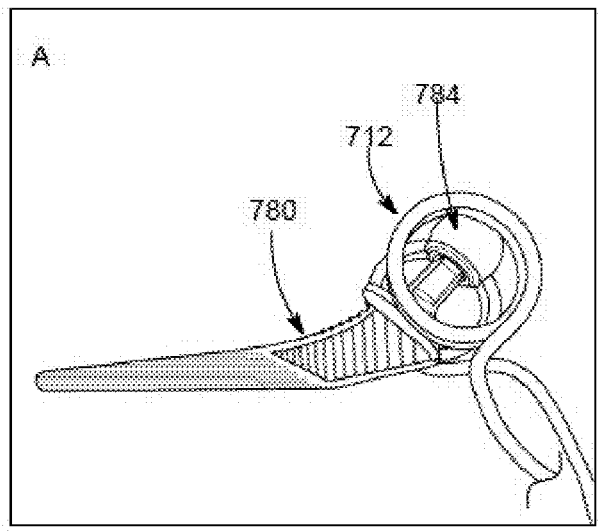

FIG. 7 shows the prosthetic implant 680 in the form of a metal implant (hip stem) similar to FIG. 8 shows the prosthetic implant 780 in the form of a metal implant (hip stem) and a narrow, rigid, water cooled hollow coil 712.

Figure 9:
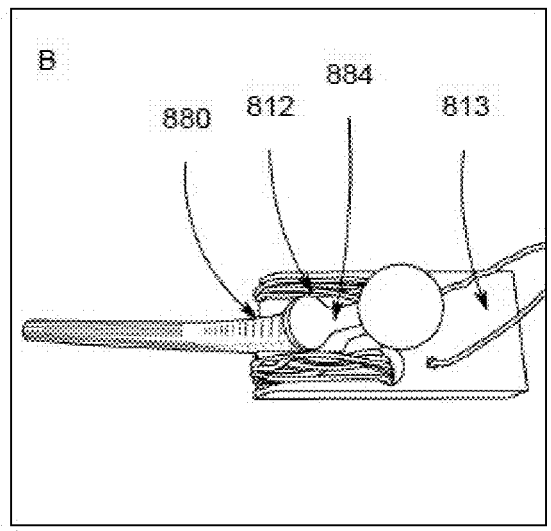

FIG. 9 shows the prosthetic implant 880 in the form of a metal implant (hip stem) and a Litz wire coil 812 and a coil holder 813. The coil holder 813 is made of electrically insulating and thermally insulating material (e.g. plastic/s and/or ceramic/s). It will be appreciated that the coil holder may be useful for in vitro and/or in vivo use, such as for positioning the coil 812 relative to the portion 884 of the prosthetic implant 880.

Figure 10:
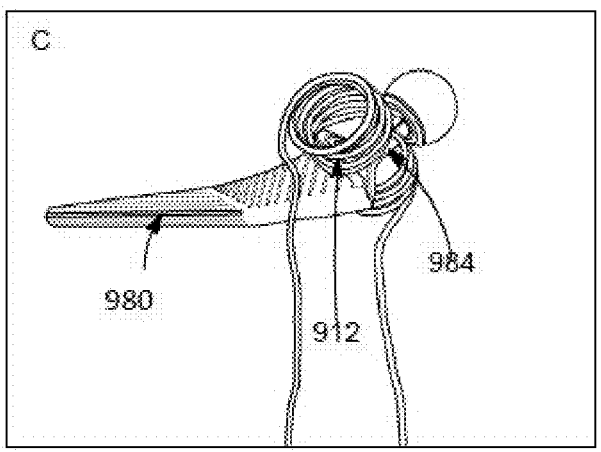

FIG. 10 shows the prosthetic implant 980 in the form of a metal implant (hip stem) and a "spring coil" 912 which is flexible to allow for manipulation during surgery for e.g. difficult to reach locations.

Figure 11:
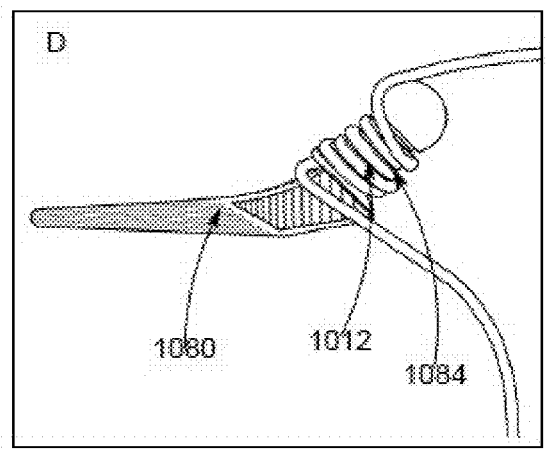

FIG. 11 shows the prosthetic implant 1080 in the form of a metal implant (hip stem) and a coil 1012 with a wire that is wrapped around the implant 1080 to create a custom coil.

It will be appreciated that the portion 384, 484, 584, 684, 784, 884, 984, 1084 of the prosthetic implant 380, 480, 580, 680, 780, 880, 980, 1080 is directly heatable by induction, with the portion 384, 484, 584, 684, 784, 884, 984, 1084 of the prosthetic implant 380, 480, 580, 680, 780, 880, 980, 1080 comprising a conductive metal material as shown here, such as one or more of: steel; titanium; an alloy/s; and/or cobalt-chromium. The coils (FIGS. 4 to 11) may also be equipped with magnetic flux concentrators to potentially enhance their efficiency.

The portion 384, 484, 584, 684, 784, 884, 984, 1084 of the prosthetic implant 380, 480, 580, 680, 780, 880, 980, 1080 comprises at least one boundary or surface configured to engage or interact or interface with tissue, such as muscle and/or bone and/or cartilage tissue, and the like. The apparatus 10, 110 is configured to directly and/or indirectly heat the boundary or surface. In at least some examples the boundary or surface comprises the conductive material. In other examples (not shown) the boundary or surface comprises a non or less conductive coating or layer, with the apparatus 10, 110 being configured to indirectly heat the coating or layer by inducing heat in the associated conductive material, such as underlying the coating or layer, with the heat being transmitted or propagated from the conductive material to or through the non or less conductive material, such as by conduction.

As shown here, in at least some examples, the coil 312 to 1012 is deformable in dependence on the portion of the prosthetic or implant. The deformation is plastic and/or elastic. The coil 312 to 1012 is configured to deform to adapt to the prosthetic implant 380 to 1080.

It will be appreciated that, when used in vivo during surgery, the apparatus 10, 110 is configured to heat the portion of the prosthetic implant 380 to 1080 during the procedure without unduly heating patient tissue. The apparatus 10, 110 is configured to heat the portion of the prosthetic implant 380 to 1080 to a temperature at or below a maximum temperature associated with tissue damage. For example, the apparatus 10, 110 is configured to heat the portion 384 to 1084 of the prosthetic implant 380 to 1080 only to temperatures unassociated with undesirable tissue damage. Here, the apparatus 10, 110 is configured to heat the portion 384 to 1084 of the prosthetic implant 380 to 1080 to a temperature at or below a minimum temperature associated with infection control. For example, the minimum temperature is associated with killing, or at least combatting, infection.

In vivo, the apparatus 10, 110 may be configured to heat the portion 384 to 1084 of the prosthetic implant 380 to 1080 to a temperature in a range from about 38° C. to 120° C., preferably of from 60° C. to about 70° C., preferably for a period of time sufficient to destroy at least 80% of the biofilm formed by one or more invasive species that cause the infection.

The apparatus 10, 110 is controlled in dependence of a temperature of the portion 384 to 1084 of the prosthetic implant 380 to 1080, and/or additional temperature/s, such as of other portion/s of the prosthetic implant 380 to 1080 and/or tissue (e.g. bone, muscle, cartilage, nerves, etc). The apparatus 10, 110 is controllable in dependence on a thermal sensor or thermometer.

Referring now to FIG. 12, there is shown a thermal image indicative of selective heating of the portion of the prosthetic implant 1180 to more than about 60 degrees Celsius, with the heating being restricted to a target portion within the coil 1112. It will be appreciated that the apparatus 10, 110 may be controllable in dependence on such a temperature measurement/s. For example, an operator may be provided with such updating real time images from an infra red thermal camera during a procedure, even with an augmented and/or a virtual reality device. Accordingly, the operator can manually adapt the heating in dependence on information the operator or user receives from the infra red thermal camera.

In other embodiments (not shown), the apparatus 10, 110 may be configured to automatically adapt the heating. Such apparatus can adapt the heating in dependence on a calculated or determined cumulative thermal dose.

In alternative methods, especially non-invasive methods, temperature measurement and control can be via patient feedback. For example, particularly in a procedure without anaesthetic, temperature measurement can be provided by an indication from the patient of warmth and/or heat and/or pain. An operator, such as a surgeon or even the patient, may adapt the provision of heat accordingly.

Examples of methods of use of the foregoing coils and/or apparatus follows.

The method comprises configuring the coil 12, 112, 212, 312, 412, 512, 612, 712, 812, 912, 1012, 1112 for direct application to the portion 384 to 1184 of the prosthetic implant 380 to 1080. The method comprises directly applying the coil 12, 112, 212, 312, 412, 512, 612, 712, 812, 912, 1012, 1112 to the portion 384 to 1184 of the prosthetic implant 380 to 1080. The method comprises directly contacting the prosthetic implant 380 to 1180 with the coil 12, 112, 212, 312, 412, 512, 612, 712, 812, 912, 1012, 1112. The method comprises transmitting energy to the portion 384 to 1184 of the prosthetic implant 380 to 1080 without the energy first passing through a patient's skin. The method comprises avoiding or at least minimising passage of energy through a patient's skin and/or tissue. The method comprises positioning the portion 384 to 1184 of the prosthetic implant 380 to 1080 within a distance from or of the coil 12, 112, 212, 312, 412, 512, 612, 712, 812, 912, 1012, 1112, the distance being less than or equal to a dimension of the coil 12, 112, 212, 312, 412, 512, 612, 712, 812, 912, 1012, 1112. The method comprises positioning the coil 12, 112, 212, 312, 412, 512, 612, 712, 812, 912, 1012, 1112 and/or the portion 384 to 1184 of the prosthetic implant 380 to 1080. For example the method comprises positioning the coil 12, 112, 212, 312, 412, 512, 612, 712, 812, 912, 1012, 1112 closer to the portion 384 to 1184 of the prosthetic implant 380 to 1080 than a diameter of the coil 12, 112, 212, 312, 412, 512, 612, 712, 812, 912, 1012, 1112. The method comprises inserting the coil 12, 112, 212, 312, 412, 512, 612, 712, 812, 912, 1012, 1112 into or through a surgical incision.

The method comprises providing the heat via the handheld apparatus 10, 110. The method comprises at least partially controlling an administration of heat, such as by controlling a power, such as an amount and/or duration of power, supplied to the induction coil 12, 112, 212, 312, 412, 512, 612, 712, 812, 912, 1012, 1112.

The method comprises providing an operating frequency of a Pulsed Electromagnetic Field (PEMF) of less than about 100 kHz.

The method comprises treating an infection, such as a prosthetic joint infection (PJI). The method comprises an infection treatment method. The method comprises at least assisting in killing bacteria. The method comprises heating bacteria to a critical temperature whereby bacteria are at least weakened, such as to assist in infection control by other means such as administered drugs and/or immuno-defence mechanisms.

Accordingly, the method may further comprise administering a drug, able to control infection, preferably a biocidal or biostatic drug, more preferably an antibiotic composition effective in reducing the active count of isolated microorganism, at a concentration at the location of the prosthetic or implant suitable to achieve a reduction of the active count of microorganisms, to at least assist in treating an infection. Preferably, the antibiotic composition comprises at least one antibiotic compound selected from the family of antibiotics comprising penicillins, cephalosporins, aminoglycosides, tetracyclines, sulfonamides, macrolide antibiotics and/or quinolones, or the group comprising imipenem, aztreonam, chloramphenicol, erythromycin, clindamycin, spectinomycin, vancomycin, rifampin, bacitracin, methenamine, tobramycin, and nitrofurantoin. Preferably, the method may comprise administering the antibiotic treatment at a dosage effective to produce a biocidal or biostatic, preferably bacteriostatic or fungistatic concentration at the biofilm site after the heating treatment. Alternatively, antibiotics, or other suitable compounds may be administered before the induction heating to enhance the effectiveness of the heat stress. Antibiotics and other compounds may also be used in between heating cycles to kill bacteria or slow down their growth in case multiple heating cycles are needed. The present invention hence also relates to a drug capable of controlling or removing an infection, preferably wherein the drug comprises a biocidal composition, for use of the treatment of infections in combination with a heat treatment according to the present invention, in patients in need thereof.

Figure 13:
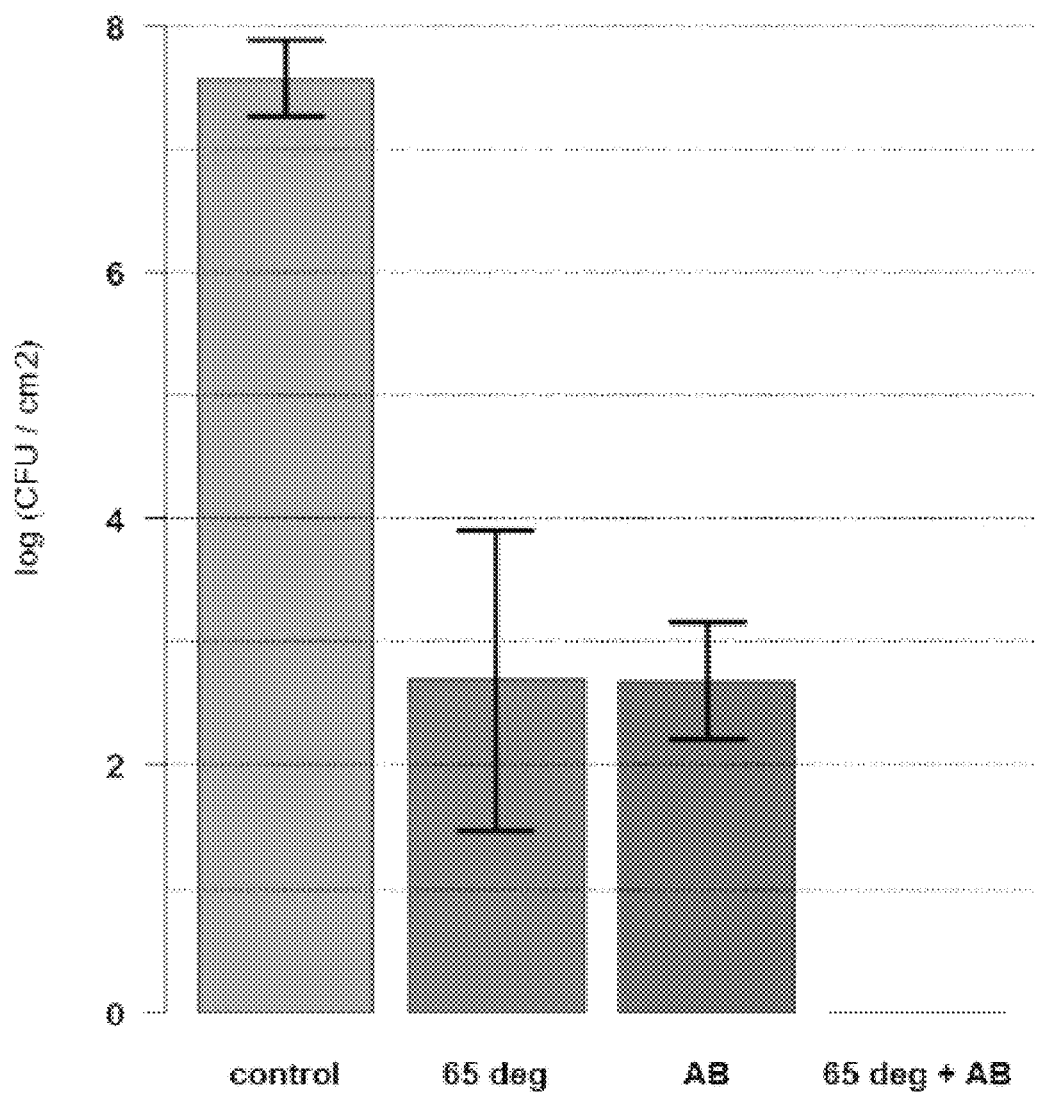
FIG. 13 shows a graph showing the full eradication of a S. *Epidermidis* biofilm from a titanium alloy coupon after a thermal shock of 65° C. from 3.5 minutes with induction heating followed by 24 hours exposure to vancomycine 10 mg/L and rifampicine 1 mg in a BHI culture medium.

FIG. 13 shows a graph showing the full eradication of a S. *Epidermidis* biofilm from a titanium alloy coupon after a thermal shock of 65° C. from 3.5 minutes with induction heating followed by 24 hours exposure to vancomycine 10 mg/L and rifampicine 1 mg in a BHI culture medium. N=6 or greater for each group. This experiment shows that there may be a synergistic effect between thermal shock and antibiotics, and the active count is expressed in Log (CFU/cm$^2$), i.e. logarithm of colony forming units per cm$^2$. Clearly, the combination of these treatments steps shows a strong synergy between a combined infection treatment method, comprising heating bacteria to a critical temperature whereby bacteria are at least weakened, and followed by an infection control by administered drugs, whereby the combination is superior to the separate treatments. It is noted that the present method also may allow to reduce the amount of antibiotic significantly.

The method comprises administering heat to a biofilm associated with the prosthetic implant 380 to 1180. Additionally, or alternatively, the method comprises heating the at least a portion 384 to 1184 of the prosthetic implant 380 to 1080 to assist in attaching and/or detaching the prosthetic implant 380 to 1180. For example the method comprises heating the portion 384 to 1184 of the prosthetic implant 380 to 1080 to expand the portion 384 to 1184 of the prosthetic implant 380 to 1080. In at least some examples, the portion 384 to 1184 of the prosthetic implant 380 to 1080 to be heated may be associated with a fixation of the prosthetic implant 380 to 1180. For example, the portion 384 to 1184 of the prosthetic implant 380 to 1080 comprises a socket or recess. The socket or recess may be associated with another portion 384 to 1184 of the prosthetic implant 380 to 1080, such as for receiving another part or component of the prosthetic implant 380 to 1180. For example, where the prosthetic implant 380 to 1180 comprises a fixture or fastening for securement, the method comprises heating the fitting or securement, or at least a portion thereof, to assist in application and/or removal of the prosthetic implant 380 to 1180. The method comprises thermally expanding and/or contracting the portion 384 to 1184 of the prosthetic implant 380 to 1080. The method comprises heating the portion 384 to 1184 of the prosthetic implant 380 to 1080 prior to and/or during attachment, connection or insertion of the portion 384 to 1184 of the prosthetic implant 380 to 1080. The method comprises heating to ease attachment, connection or insertion, such as by thermally adapting clearances or tolerances to provide for a looser fit during attachment, connection or insertion. The method comprises subsequent cooling, such as passive cooling, to thermally adapt clearances or tolerances to provide for a tighter fit when attached, connected or inserted. The method comprises heating the portion 384 to 1184 of the prosthetic implant 380 to 1080 during temporary or permanent removal or loosening of the prosthetic implant 380 to 1180, such as during an invasive procedure. The method comprises heating the portion 384 to 1184 of the prosthetic implant 380 to 1080 to loosen the prosthetic implant 380 to 1180. In at least some examples, the method comprises sequentially and/or cyclically thermally expanding and contracting the portion 384 to 1184 of the prosthetic implant 380 to 1080.

The method comprises weakening a fastening for or of the prosthetic implant 380 to 1180, such as for assisting in the temporary or permanent removal of the portion 384 to 1184 of the prosthetic implant 380 to 1080. For example, where a prosthetic implant 380 to 1180 has been secured, such as directly or indirectly to a bone, the method comprises weakening an interface between the prosthetic implant 380 to 1180 and the bone. The method comprises weakening a bond, such as with a bonding means or agent, between the prosthetic implant 380 to 1180 and the patient.

The method comprises heating the portion of the prosthetic of implant in vitro prior to insertion or application of the portion 384 to 1184 of the prosthetic implant 380 to 1080 to the patient. Additionally or alternatively, the method comprises heating the portion 384 to 1184 of the prosthetic implant 380 to 1080 in vivo, whilst the portion 384 to 1184 of the prosthetic implant 380 to 1080 is attached to, or located in, the patient—or being attached to, or being located in the patient.

In at least some examples, the method comprises heating the portion 384 to 1184 of the prosthetic implant 380 to 1080 during a surgical procedure. The method comprises an invasive surgical procedure. Alternatively, the method comprises a non-invasive procedure. The method comprises a treatment of the prosthetic implant 380 to 1180, but not a treatment of the patient as such.

The method comprises in vivo use. The method comprises heating the portion 384 to 1184 of the prosthetic implant 380 to 1080 whilst the portion 384 to 1184 of the prosthetic implant 380 to 1080 is located in and/or attached to a body. Additionally or alternatively, the method comprises ex vivo use. The method comprises in vitro use. The method comprises heating the portion 384 to 1184 of the prosthetic implant 380 to 1080 whilst the portion 384 to 1184 of the prosthetic implant 380 to 1080 is located outside and/or detached from the body. In at least some examples, the method comprises heating the portion 384 to 1184 of the prosthetic implant 380 to 1080 ex vivo during a surgical procedure, such as where the prosthetic implant 380 to 1180 (or portion thereof) is detached and/or removed from the body.

The method comprises heating the portion 384 to 1184 of the prosthetic implant 380 to 1080 during the surgical procedure without unduly heating patient tissue. The method comprises heating the portion 384 to 1184 of the prosthetic implant 380 to 1080 to a temperature at or below a maximum temperature. The maximum temperature may be associated with tissue damage. For example, the method comprises heating the portion 384 to 1184 of the prosthetic implant 380 to 1080 only to temperatures unassociated with undesirable tissue damage. The method comprises preventing or at least minimising tissue damage.

The method comprises heating the portion 384 to 1184 of the prosthetic implant 380 to 1080 to a temperature at or below a minimum temperature. The minimum temperature may be associated with infection control. For example, the minimum temperature may be associated with killing, or at least combatting, infection. The method comprises heating the portion 384 to 1184 of the prosthetic implant 380 to 1080 to a temperature in a range, such as in a range from about 65° C. to about 70° C.

The method comprises heating the portion 384 to 1184 of the prosthetic implant 380 to 1080 to a target temperature. The method comprises controlling heating in dependence of a temperature of the portion 384 to 1184 of the prosthetic implant 380 to 1080, and/or additional temperature/s, such as of other portion/s of the prosthetic implant 380 to 1180 and/or tissue (e.g. bone, muscle, cartilage, nerves, etc). The method comprises controlling heating in dependence on a thermal sensor or thermometer. The method comprises direct temperature measurement/s. The method comprises operating a temperature measurement device. The method comprises providing an augmented and/or a virtual reality. The method comprises adapting the heating, such as via the power output to or from the coil 12, 112, 212, 312, 412, 512, 612, 712, 812, 912, 1012, 1112, in dependence on the temperature measurement device. The method comprises automatically adapting the heating. Additionally, or alternatively, the method comprises manually adapting the heating. For example, the method comprises an operator or user of the device manually adapting the heating in dependence on information the operator or user receives from the temperature measurement device. The method comprises real time visualisation and/or measurement, such as provided by a display connected to or associated with an infra-red thermal camera. The method comprises adapting the heating in dependence on a cumulative thermal dose. The method comprises calculating the cumulative thermal dose real time. The method comprises displaying the temperature/s and/or cumulative thermal dose/s to the user or operator, such as a surgeon. In at least some examples, the method comprises automatically adapting the heating with an integral thermal sensor and a (micro-)controller comprised in the heating apparatus 10, 110.

The method comprises heating only a portion 384 to 1184 of the prosthetic implant 380 to 1080. For example, the method comprises not heating the entire prosthetic implant 380 to 1180. The method comprises inducing heat in only a single portion 384 to 1184 of the prosthetic implant 380 to 1080 at a time. The method comprises not heating the entire prosthetic implant 380 to 1180 simultaneously.

The method comprises selectively heating the portion 384 to 1184 of the prosthetic implant 380 to 1080. The method comprises selectively heating only part of the implant that is safe. The method comprises selectively heating only part of the implant that is no or low-risk. The method comprises avoiding heating areas of the implant associated with bone fixation (e.g. for total joint replacements); and/or areas of the prosthetic implant 380 to 1180 in proximity to or associated with important anatomical structures such as nerves (e.g. in case of infected plate in elbow). Alternatively, high risk areas (e.g. for loss of bone fixation or proximity of nerves/vessels) are heated at or to a lower temperature/s (e.g. relative to low risk areas). The method comprises targeting only the portion 384 to 1184 of the prosthetic implant 380 to 1080 to be heated, such as with a precision coil 12, 112, 212, 312, 412, 512, 612, 712, 812, 912, 1012, 1112.

The method comprises inductively heating a first portion 384 to 1184 of the prosthetic implant 380 to 1080, whilst not inductively heating a second portion 384 to 1184 of the prosthetic implant 380 to 1080. The method comprises allowing heat transfer from the first portion 384 to 1184 of the prosthetic implant 380 to 1080 to the second portion 384 to 1184 of the prosthetic implant 380 to 1080. The method comprises utilising the second portion 384 to 1184 of the prosthetic implant 380 to 1080 as a heat sink for the first portion 384 to 1184 of the prosthetic implant 380 to 1080. Additionally or alternatively, the method comprises cooling, such as actively cooling, the coil 12, 112, 212, 312, 412, 512, 612, 712, 812, 912, 1012, 1112; and/or the portion of the prosthetic and/or other portion/s of the prosthetic implant 380 to 1180; and/or patient tissue.

The method comprises sequentially heating two or more portions of the prosthetic implant 380 to 1180, such as by heating a first portion prior to heating a second portion 384 to 1184 of the prosthetic implant 380 to 1080.

In at least some examples, the method comprises heating the entire prosthetic implant 380 to 1180 380 to 1180.

The method comprises sterilisation. The method comprises sterilisation using a sterilisation device for sterilising surgical equipment, such as standard sterilising device for sterilising the likes of a surgical drill, surgical saw or the like. The sterilisation comprises one or more of: autoclaving; dry heat; chemical sterilant/s; mechanical and/or ultrasonic cleaning.

In at least some examples, the method comprises deforming the coil 12, 112, 212, 312, 412, 512, 612, 712, 812, 912, 1012, 1112 in dependence on the portion 384 to 1184 of the prosthetic implant 380 to 1080. The deformation is plastic and/or elastic. The method comprises deforming the coil 12, 112, 212, 312, 412, 512, 612, 712, 812, 912, 1012, 1112 to adapt to the prosthetic implant 380 to 1180. The method comprises deforming the coil 12, 112, 212, 312, 412, 512, 612, 712, 812, 912, 1012, 1112 by the prosthetic implant 380 to 1180, such as by forcing the coil 12, 112, 212, 312, 412, 512, 612, 712, 812, 912, 1012, 1112 or prosthetic implant 380 to 1180 against the other of the coil 12, 112, 212, 312, 412, 512, 612, 712, 812, 912, 1012, 1112 or prosthetic/implant. The method comprises deforming the coil 12, 112, 212, 312, 412, 512, 612, 712, 812, 912, 1012, 1112 by manipulation by the user. For example, the method comprises the user plastically and/or elastically deforming the coil 12, 112, 212, 312, 412, 512, 612, 712, 812, 912, 1012, 1112 to adapt to a shape of a particular prosthetic implant 380 to 1180.

The method comprises heating the prosthetic implant 380 to 1180 for implantation into and/or attachment to a human body. Alternatively, the method comprises heating the prosthetic implant 380 to 1180 for implantation into and/or attachment to a non-human body, such as a non-human mammal. The method comprises implanting and/or attaching the prosthetic implant 380 to 1180. Additionally, or alternatively, the method comprises removing and/or detaching the prosthetic implant 380 to 1180.

Whilst specific embodiments of the present invention have been described above, it will be appreciated that departures from the described embodiments may still fall within the scope of the present invention.

It will be appreciated that any of the aforementioned apparatus may have other functions in addition to the mentioned functions, and that these functions may be performed by the same apparatus.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims.

The applicant indicates that aspects of the present invention may consist of any such individual feature or combination of features. It should be understood that the embodiments described herein are merely exemplary and that various modifications may be made thereto without departing from the scope or spirit of the invention.

The invention claimed is:

1. A medical inductive heating apparatus configured for heating at least a portion of a prosthetic or implant to a temperature and for a time suitable for reducing the active count of invasive cell species forming a biofilm, the apparatus comprising at least one external induction coil and a temperature measurement device configured to calculate a cumulative thermal dose, the external induction coil being external to a body or housing of the apparatus, wherein the coil is sized and dimensioned to be smaller than a body portion associated with the prosthetic or implant;
wherein the apparatus is configured to provide an operating frequency of a Pulsed Electromagnetic Field (PEMF) of less than 100 kHz, and
wherein the prosthetic or implant is a load-bearing prosthetic or implant.

2. The apparatus of claim 1, wherein the apparatus is configured to heat the portion of the prosthetic or implant to a temperature in a range from about 38° C. to about 120° C. for a period of time of at least 3.5 minutes to reduce the active count of invasive cell species forming a biofilm.

3. The apparatus of claim 1, wherein the apparatus is configured to position the coil closer to the portion of the prosthetic or implant than a diameter of the coil.

4. The apparatus of claim 1, wherein the coil is configured for insertion into or through a surgical incision.

5. The apparatus of claim 1, wherein the apparatus comprises a portable, handheld apparatus configured for single-handed use by a user, the apparatus comprising a pistol grip handle with an actuator for operation by the gripping hand.

6. The apparatus of claim 1, wherein the apparatus is configured to heat the at least a portion of the prosthetic or implant to assist in attaching and/or detaching the prosthetic or implant by thermally expanding and/or contracting the portion of the prosthetic or implant.

7. The apparatus of claim 1, wherein the apparatus is configured to heat the portion of the prosthetic or implant in vivo, whilst the portion of the prosthetic or implant is attached to, or located in, the patient.

8. The apparatus of claim 1, wherein the apparatus is configured to heat the portion of the prosthetic or implant ex vivo during a surgical procedure.

9. The apparatus of claim 1, wherein the apparatus is configured to selectively heat only a portion of the prosthetic or implant; and to not heat the entire prosthetic or implant, the apparatus is configured to inductively heat a first portion of the prosthetic or implant, whilst not inductively heating a second portion of the prosthetic or implant, to allow heat transfer from the first portion of the prosthetic or implant to the second portion of the prosthetic or implant, to utilize the second portion of the prosthetic or implant as a heat sink for the first portion of the prosthetic or implant.

10. The apparatus of claim 1, wherein the coil is deformable in dependence on the portion of the prosthetic or implant.

11. An assembly for heating at least a portion of a prosthetic or implant, the assembly comprises the apparatus of claim 1 and the at least a portion of the prosthetic or implant, wherein the assembly comprises a temperature control mechanism.

12. A method of inductively heating at least a portion of a prosthetic or implant with an apparatus, the method comprising:
sizing and dimensioning at least one external induction coil to be smaller than a body portion associated with the prosthetic or implant;
inductively heating at least the portion of the prosthetic or implant to a temperature and reducing the active count of invasive cell species forming a biofilm;
calculating a cumulative thermal dose in real-time; and
adapting the heating in dependence on the cumulative thermal dose,
the apparatus comprising at least one external induction coil, the external induction coil being external to a body or housing of the apparatus, wherein the coil is sized and dimensioned to be smaller than a body portion associated with the prosthetic or implant, and
wherein the prosthetic or implant is a load-bearing prosthetic or implant.

13. The method of claim 12, wherein the method comprises in vitro heating.

14. The method of claim 12, wherein the method comprises ex vivo heating.

15. The method of claim 12, wherein the method comprises in vivo heating, wherein the method comprises inserting the coil into or through a surgical incision.

16. The method of claim 12, wherein the method comprises configuring the coil to directly heat only the portion of the prosthetic or implant.

17. The method of claim 12, wherein the method comprises treating an infection.

18. The method of claim 12, wherein the method comprises heating the at least a portion of the prosthetic or implant to assist in attaching and/or detaching the prosthetic or implant.

19. The method of claim 12, further comprising administering a biocidal, antibiotic composition effective in reducing the active count of invasive species at a concentration at the location of the prosthetic or implant suitable to achieve a reduction of the active count of microorganisms, wherein the biocidal antibiotic composition comprises at least one antibiotic compound selected from the family of antibiotics comprising penicillins, cephalosporins, aminoglycosides, tetracyclines, sulfonamides, macrolide antibiotics and/or quinolones.

20. A medical inductive heating apparatus configured for heating at least a portion of a prosthetic or implant to a temperature in a range from about 38° C. to about 120° C., the apparatus comprising at least one external induction coil and a temperature measurement device configured to calculate a cumulative thermal dose, the external induction coil being external to a body or housing of the apparatus,
wherein the coil is sized and dimensioned to be smaller than a body portion associated with the prosthetic or implant,
wherein the apparatus is configured to provide an operating frequency of a Pulsed Electromagnetic Field (PEMF) of less than 100 kHz, and
wherein the prosthetic or implant comprises a joint prosthetic or implant.

21. The apparatus of claim 20, wherein the apparatus is configured to heat the portion of the prosthetic or implant to a temperature in a range from about 38° C. to about 120° C., for a period of time of at least 3.5 minutes to reduce the active count of invasive cell species forming a biofilm.

\* \* \* \* \*